United States Patent [19]

Tomomasa et al.

[11] Patent Number: 5,750,094
[45] Date of Patent: May 12, 1998

[54] LIPSTICK OVERCOAT COMPOSITION

[75] Inventors: Satoshi Tomomasa; Tomiyuki Nanba; Yoshikazu Soyama, all of Yokohama, Japan

[73] Assignee: Shiseido Company, Ltd., Tokyo, Japan

[21] Appl. No.: 451,089

[22] Filed: May 25, 1995

[30] Foreign Application Priority Data

May 24, 1994 [JP] Japan .................................. 6-110859
May 25, 1994 [JP] Japan .................................. 6-110858

[51] Int. Cl.$^6$ .................. A61K 7/025; A61K 31/695; A61K 31/08
[52] U.S. Cl. .................. 424/64; 514/63; 514/722; 514/723
[58] Field of Search .................. 424/64; 514/63, 514/722, 723

[56] References Cited

U.S. PATENT DOCUMENTS 4,803,067  2/1989  Brunetta et al. .................. 424/63

FOREIGN PATENT DOCUMENTS

| 0 494 412 A2 | 7/1992 | European Pat. Off. . |
| 61-24512 | 2/1986 | Japan . |
| 61-12883 | 6/1986 | Japan . |
| 52-21829 | 8/1993 | Japan . |

OTHER PUBLICATIONS

CAPLUS Abstract 1993: 11517, Mellul et al (1992).

WPIDS Abstract 95: 012122, JP 06299190 (1993).

Japanese Abstract JP-A-107 053 328, Hokao EMI, Feb. 28, 1995.

*Primary Examiner*—Marianne M. Cintins
*Assistant Examiner*—M. Moezie
*Attorney, Agent, or Firm*—Sprung Kramer Schaefer & Briscoe

[57] ABSTRACT

An O/W type lipstick overcoat composition comprising (i) 2 to 80% by weight of a dimethyl polysiloxane, and/or a perfluoro polyether in an inner phase; and (ii) (a) water and (b) a silica powder and/or alumina powder in an outer phase or a W/O type lipstick overcoat composition (i) 40 to 70% by weight of a dimethyl polysiloxane in an outer phase and (ii) (a) water and (b) a silica powder and/or alumina powder in an inner phase.

2 Claims, No Drawings

LIPSTICK OVERCOAT COMPOSITION

BACKGROUND OF THE INVENTION

1. Field of the Invention

The present invention relates to a lipstick overcoat composition. More particularly, it relates to a lipstick overcoat composition which, by coating after application of a lipstick, is capable of improving the sustainability of the cosmetic effect of the lipstick and keeps down marks on cups, glasses, etc.

2. Description of the Related Art

Lipstick overcoat compositions are now being marketed as a product aimed at improving the sustainability of the cosmetic effect of lipsticks and the luster thereof.

In the past, there have been known lipstick overcoat compositions obtained by mixing with water or alcohol a cellulosic polymer compound, vinyl resin, acryl resin, or other polymer compound, methylphenyl polysiloxane, etc. and making use of the characteristics of the mixed polymer compound etc. and overcoats of a powder or pressed form comprised primarily of a powder mixed with an oil component (Japanese Examined Patent Publication (Kokoku) No. 61-12883 and Japanese Unexamined Patent Publication (Kokai) No. 61-24512).

However, the conventional lipstick overcoat compositions have not been sufficiently satisfactory in terms of preventing lipstick marks on cups, glasses, etc. Further, the powder types end up uneven in effect depending on the method of application and the types containing polymer compounds etc. result in a sticky feeling at the time of use and therefore were problematic in terms of user satisfaction.

Accordingly, there has been a need for a lipstick overcoat composition which can improve the sustainability of the cosmetic effect of the lipstick and suppress lipstick marks and is superior in ease of use.

Further, there have been types which aim at the effect of the prevention of secondary adhesion by dispersing a powder of silica, alumina, etc. in perfluoro polyether and making use of the oil repulsion of the perfluoro polyether (Japanese Unexamined Patent Publication (Kokai) No. 5-221829). This technique has the effect of improving the sustainability of the cosmetic effect, the effect of suppressing lipstick marks, and the effect of improving the ease of use, but the powder is difficult to disperse in the perfluoro polyether and therefore the two easily separate. Therefore there are the problem that, even at room temperature, only the perfluoro polyether will sometimes come out when the overcoat is squeezed from the tube, and the problem that even after application over the lipstick the silica powder will separate along with time and result in the lipstick appearing to be sprinkled with white specks or taking on a marked matt-like appearance.

SUMMARY OF THE INVENTION

Accordingly, the objects of the present invention are to provide a lipstick overcoat composition which is capable of improving the sustainability of the cosmetic effect, suppresses lipstick marks, is superior in ease of use, and, further, is free from the problem of just perfluoropolyether coming out when squeezing the overcoat out of the tube and from the separation of the silica powder over time after application on the lipstick and the resultant appearance of white specks on the lipstick.

Other objects and advantages of the present invention will be apparent from the following description.

In accordance with the present invention, there is provided an oil-in-water (O/W) type lipstick overcoat composition comprising:

(i) 2 to 80% by weight of at least one compound selected from the group consisting of:

(a) dimethyl polysiloxanes having the formula (I):

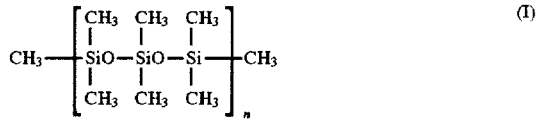

wherein n is 26–600 on average, and (b) perfluoro polyethers having the formula (II):

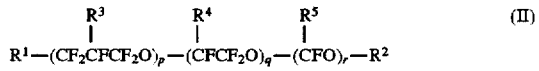

wherein, $R^1$, $R^2$, $R^3$, $R^4$, and $R^5$ are the same or different and represent a fluorine atom, a perfluoroalkyl group, or an oxyperfluoroalkyl group and p, q, and r are independently integers of 0 or more giving a molecular weight of 500 to 10,000, provided that p=q=r=0 never occurs, in an inner phase; and (ii) (a) water and (b) at least one powder selected from the group consisting of silica powder and alumina powder in an outer phase.

In accordance with the present invention, there is also provided water-in-oil (W/O) type lipstick overcoat composition comprising:

(i) 40 to 70% by weight of dimethyl polysiloxane having the above-mentioned formula (I) in an outer phase; and (ii) (a) water and (b) at least one powder selected from the group consisting of silica powder and alumina powder in an inner phase.

DESCRIPTION OF THE PREFERRED EMBODIMENTS

The present invention will now be explained in more detail.

In the present invention, the aqueous phase includes silica powder and/or alumina powder, so it is possible to cause the liquid oil component of the lipstick to solidify due to the oil-absorbing action of the powder after application and thereby enable a sustained cosmetic effect.

However, with just inclusion of silica powder and/or alumina powder in the aqueous phase, the powder will eventually appear as white specks on the lipstick and the lipstick will become matt-like in appearance. To prevent this, in the present invention, dimethyl polysiloxane and/or perfluoro polyether, which has poor affinity with the lipstick, are mixed in as an oil component, whereby it is possible to obtain a paste-like form and thereby to obtain a lipstick overcoat composition, which is capable of improving the sustainability of the cosmetic effect of the lipstick, of suppressing lipstick marks on cups, glasses, etc. and smearing, and further of being easy to use.

The first embodiments of the present invention will be explained below according to the constituent requirements.

(i) Inner Phase (i.e., Oil component)

(a) Dimethyl Polysiloxane

The dimethyl polysiloxane has the above-mentioned general formula (I) and has an average n of 26 to 600.

The viscosity is preferably 20 cs to 5000 cs. In particular, in the case of the O/W type composition, a viscosity of 100 to 1000 cs is preferred from the viewpoint of the "slip" at the time of use and the smearing with lips.

More specifically, Shin-Etsu Silicone's KF96A-20 cs, 100 cs, 300 cs, 1000 cs, and 5000 cs, Toray-Dow Corning Silicone's SH200c-20 cs, 50 cs, 100 cs, 200 cs, 350 cs, 500 cs, 1000 cs, 3000 cs, and 5000 cs correspond to this.

(b) Perfluoro Polyether

The perfluoro polyether used in the present invention has the above-mentioned general formula (II).

Note that in the formula (II), the per-fluoro groups shown in parentheses do not have to be arranged in that order. Further, either random polymerization or block polymerization is possible. As the perfluoro polyether, a liquid one with a viscosity of 5 to 5000 cSt is preferable. For example, FONBLIN HC (average molecular weight of 1500), FONBLIN HC-25 (average molecular weight of 3200), and FONBLIN HC-R (average molecular weight of 6600) of the following formula (III) (all made by Montefluos Co.), Demnum S-20 (average molecular weight of 25,000), Demnum S-65 (average molecular weight of 4500), Demnum S-100 (average molecular weight of 5600), and Demnum S-200 (average molecular weight of 8400) of the following formula (IV) (all made by Daikin Industries), and other commercially available products may be used.

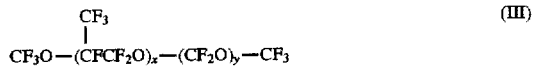

(III)

wherein, x and y are integers giving a molecular weight of 500 to 10,000 and y/x is 0.2 to 2.

(IV)

wherein l is an integer of 4 to 500.

Note that it is possible to include either of dimethyl polysiloxane and perfluoro polyether or simultaneously include both in the first embodiment of the present invention.

These oil components are contained in an amount of 2 to 80% by weight (Note: over 80% by weight, the oil-in-water (O/W) type emulsification is not possible). Further, an oil component of 5 to 80% by weight is preferable in view of the further improvement of the gloss (luster) after application. Also, 5 to 70% by weight is more preferable to improve the smoothness of use.

(ii) Outer Phase (aqueous phase)

The aqueous phase includes (a) water and (I) silica powder and/or alumina powder.

The silica powder and alumina powder contained in the outer aqueous phase may be any powder normally used for cosmetics. For example, use may be suitably made of Sairoid 55 (made by Fuji-Devinson), Aerosil 200, 300, R-972, R974 (made by Fuji Kasei), Alumina AKS-G, AKP-30: AKP-GM (made by Sumitomo Chemical), etc.

These silica powder and alumina powder may be used alone or in combinations of two or more types. They are preferably included in an amount of 0.5 to 10% by weight, more preferably 1 to 10% by weight, still more preferably 1 to 5% by weight in the entire composition.

When the powder is less than 0.5% by weight, a remarkable effect cannot be obtained, while when the powder is 10% by weight, the hardness becomes high and application becomes difficult. Under 5% by weight, there is the effect of improvement of the ease of application.

Note that it is difficult to cause a silica powder having a hydrophobic surface as represented by Aerosil R-972 and R974 and alumina powder to disperse as they are in water. By using the method of first moistening the powder with a suitable amount of ethanol or polyhydric alcohol etc. and then stirring and dispersing it while adding water, the powder can be easily made to disperse in the water phase. Note that this method was also newly discovered by the present inventors.

Further, the lipstick overcoat composition of the present invention can include a water-soluble emulsifying agent in the water phase to cause emulsification. Any water-soluble emulsifying agent which is generally used for cosmetics can be used.

Further, the lipstick overcoat composition of the present invention takes the form of a paste with the above components, but may also be given thixotropy to improve the ease of use (ease of application on the lipstick and non-drip property) or may have various water-swelling viscous minerals or water-soluble polymers mixed in the water phase to reduce the repulsion from the lipstick when it is applied. Any thickners which are generally used for cosmetics may be used. One or two or more types may be used.

Further, in the present invention, in addition to the above essential components, components normally used in cosmetics, for example, hydrocarbons, higher fatty acid esters, animal and vegetable oils and fats, and other cosmetic use oily agents, surfactants, antioxidants, flavors, colors, alcohol, polyhydric alcohols, preservatives, ultraviolet ray absorbers, moistening agents, and water may be suitably mixed in to an extent not impairing the effect of the present invention.

The second embodiments of the present invention will be explained below according to the constituent requirements.

(i) Outer Phase (i.e., Oil component)

The dimethyl polysiloxane has the above-mentioned general formula (I) and has an average n of 26 to 600, the dimethyl polysiloxane useable in the present embodiment is the same as that of the first embodiment of the present invention explained above.

The viscosity is preferably 20 to 1000 cs. In particular, in the case of the O/W type composition, a viscosity of 100 to 500 cs is preferred from the viewpoint of the "slip" at the time of use and the smearing with lips.

The oil component is contained in an amount of 40 to 70% by weight, in the entire composition, preferably 40 to 60% by weight since the effect is more remarkably manifested.

Further, to obtain a water-in-oil (W/O) type emulsion, an emulsifying agent is mixed in. As the emulsifying agent, any general emulsifying agent able to be dispersed in silicone oil may be used. For example, mention may be made of a general polyether-modified silicone oil (more specifically, for example, Toray-Down Corning Silicone's SH3746, SH3771C, SH2772C, SH3773C, SH3775C, SH3648, and SH3749 and Shin-Etsu Chemical's SC9450, KF351, and KF945A). One or more types of these may be used.

Further, to improve the stability against separation, it is possible to add an organic modified clay mineral or a powder treated to be hydrophobic etc. These may be suitably mixed in to an extent not impairing the effect of the present invention.

(ii) Inner Phase (aqueous phase)

The silica powder and alumina powder contained in the inner water phase may be any powder normally used for cosmetics, as explained above. These silica powder and alumina powder may be used alone or in combinations of two or more types. They are preferably included in an amount of 0.5 to 10% by weight with respect to the overall composition, more preferably 1 to 10% by weight, still more preferably 1 to 5% by weight.

When the powder is less than 0.5% by weight, a remarkable effect cannot be obtained, while, when the powder is more than 10% by weight, application becomes difficult. Under 5% by weight, there is the effect of improvement of the ease of application.

Note that when considering the adsorption of the powder to the lipstick, a silica powder having a hydrophobic surface as represented by Aerosil R-972 and R974 is preferred. However, it is difficult to cause such a hydrophobic powder to disperse in water. By using the method of first moistening the powder with a suitable amount of ethanol or polyhydric alcohol etc. and then stirring and dispersing it while adding water, the powder can be easily made to disperse in the water phase. Note that this method was also newly discovered by the present inventors.

Further, the lipstick overcoat composition of the present invention can include a water-soluble emulsifying agent in the water phase to cause emulsification. Any water-soluble emulsifying agent which is generally used for cosmetics can be used.

The aqueous phase is preferably 30 to 60% by weight of the entire weight, more preferably 40 to 60% by weight.

When the water phase is less than 30% by weight, the oil component is too large and dripping occurs from the lips due to insufficient viscosity. A suitable viscosity is obtained at 40% or more. Over 60% by weight, the oil does not form a continuous phase and w/o emulsification is not possible.

Further, the lipstick overcoat composition of the present invention takes the form of a paste with the above components, but may also be given thixotropy to improve the ease of use (ease of application on the lipstick and non-drip property) or may have various water-swelling viscous minerals or water-soluble polymers mixed in the water phase to reduce the repulsion from the lipstick when it is applied. Any thickners which are generally used for cosmetics may be used. One or two or more types may be used.

Further, in the both embodiments of the present invention, in addition to the above essential components, components normally used in cosmetics, for example, hydrocarbons, higher fatty acid esters, animal and vegetable oils and fats, and other cosmetic use oily agents, surfactants, antioxidants, flavors, colors, alcohol, polyhydric alcohols, preservatives, ultraviolet ray absorbers, moistening agents, and water may be suitably mixed in to an extent not impairing the effect of the present invention.

EXAMPLES

The present invention will now be further illustrated by, but is by no means limited to, the following Examples, wherein all parts and percentages are expressed on a weight basis unless otherwise noted.

Examples I-1 to I-6 and Comparative Examples I-1 to I-4

The lipstick overcoats of the compositions shown in Table I-1 were prepared by the following method:

Example I-1 to Example I-6

Polyoxyethylene (15 mole addition) laurylether was heated and dissolved in ethanol, then water was added and dispersion caused by a disperser. When adding a water-swelling viscous mineral, this was added to the mixture and further dispersion caused by a disperser. The oil component was added to this and dispersion sufficiently caused by a disperser.

Comparative Example I-1 and I-2

Polyoxyethylene (15 mole addition) laurylether was heated and dissolved in water, then the oil component was added while stirring.

Comparative Example I-3

Polyoxyethylene (15 mole addition) laurylether was heated and dissolved in ethanol, then silica was moistened and disperse caused, water was added, and dispersion was caused by a disperser. The oil component was added to this and dispersion sufficiently caused by a disperser.

Comparative Example I-4

Ethanol was added to water and then the same procedure was followed as in Comparative Example I-1 and Comparative Example I-2.

TABLE I-1

|  | Comparative Example | | | | Example | | | | | |
| --- | --- | --- | --- | --- | --- | --- | --- | --- | --- | --- |
|  | I-1 | I-2 | I-3 | I-4 | I-1 | I-2 | I-3 | I-4 | I-5 | I-6 |
| Dimethyl polysiloxane | 20 *1 | — | 1 *1 | 60 *1 | 20 *1 | — | 3 *1 | 60 *1 | 20 *2 | 20 *3 |
| Perfluoro polyether (FOMBLIN HC25) | — | 20 | — | — | — | 20 | — | — | — | — |
| Silica-alumina | — | — | 2 *4 | — | 1 *4 | 1 *4 | 1 *4 *5 | 2 *4 | 1 *4 | 1 *5 |
| Water | 79 | 79 | 86 | 29.8 | 73 | 73 | 87.5 | 32 | 69 | 69 |
| Polyoxyethylene (15 mole) lauryl ether | 1 | 1 | 1 | 1 | 1 | 1 | 0.5 | 1 | 1 | 1 |

TABLE I-1-continued

| | Comparative Example | | | | Example | | | | | |
|---|---|---|---|---|---|---|---|---|---|---|
| | I-1 | I-2 | I-3 | I-4 | I-1 | I-2 | I-3 | I-4 | I-5 | I-6 |
| Ethanol | — | — | 10 | 10 | 5 | 5 | 5 | 5 | 5 | 5 |
| Water-swelling clay mineral | — | — | — | — | — | — | 3 | — | 3 | 3 |
| Polyvinyl alcohol | | | | | | | | | 1 | 1 |
| Preservative | *6 | *6 | *6 | *6 | *6 | *6 | *6 | *6 | *6 | *6 |

*1: KF96A300;
*2: KF96A100;
*3: KF96A1000;
*4: Silica (Aerosil R972);
*5: Alumina; (Alumina AKS);
*6: Suitable quantity

Comparative Example I-5

A lipstick overcoat was produced by the following formula and the following production method:

| | | (wt %) |
|---|---|---|
| (1) | Perfluoro polyether (FOMBLIN HC-25) | 98.8 |
| (2) | Silica (Aerosil 300) | 1.0 |
| (3) | Red No. 202 | 0.1 |
| (4) | Flavor | 0.1 |

Method of Production

The components (2) to (4) were added to the component (1) and homogeneously mixed to produce a lipstick overcoat.

The lipstick mark prevention effect and sustainability of the cosmetic effect plus the ease of use of the lipstick overcoats of Examples I-1 to I-6 and Comparative Examples I-1 to I-5 were evaluated by the following test methods. The results of the evaluation are shown in Table I-2.

Test Methods

Lipstick Mark Prevention Effect

Lipstick was applied two times to the lips, then the lipstick overcoat was applied over it. A sheet of glass was then pressed against the lips to evaluate the lipstick marks. A superior lipstick mark prevention effect was indicated by o, a moderate effect by Δ, and no effect by x.

Sustainability of Cosmetic Effect

Panel members were asked to go through their day as usual, apply lipstick to their lips, apply the lipstick overcoat on top, and evaluate the adhesiveness of the cosmetic after half a day. A superior effect was indicated by o, a moderate effect by Δ, and no effect by x. Note that one of the aspects of adhesiveness of a cosmetic is the so-called smearing, that is, blurring of the contours of the lipstick along with time. This was also included in the evaluation.

Ease of Use

Lipstick was applied, the lipstick overcoat of the examples and comparative examples were applied over it, and an evaluation was made of the ease of application, the homogeneity of the cosmetic film, and other aspects of ease of use. A good ease of use was indicated by o, some problems, but usable by Δ, and total inability of use by x.

TABLE I-2

| | Comparative Example | | | | | Example | | | | | |
|---|---|---|---|---|---|---|---|---|---|---|---|
| | I-1 | I-2 | I-3 | I-4 | I-5 | I-1 | I-2 | I-3 | I-4 | I-5 | I-6 |
| Lipstick mark prevention effect | x | x | O | x | O | O | O | O | O | O | O |
| Sustainability of cosmetic effect | x | x | Δ | x | O | O | O | O | O | O | O |
| Ease of use | x <1> | x <1> | <2> | Δ <3> | x <4> | O | O | Δ <3> | O | O | O |

<1> Repulsion from the lipstick when it is applied.
<2> White specks appear around lips
<3> Somewhat hard to apply to lips
<4> Separation and white specks appearing in lipstick As clear from the results shown in Table I-2, the present embodiment is superior in each of the lipstick mark prevention effect, sustainability of the cosmetic effect, and ease of use.

Example I-7

In this example, an investigation was made of the relation between the content of the dimethyl polysiloxane shown in the general formula (I) and/or the perfluoro polyether shown in the general formula (II) and various properties and the relation between the content of the silica powder and/or alumina powder and various properties.

The lipstick overcoats of the composition shown in Table I-3 were prepared by the following method:

First, polyoxyethylene (15 mole addition) laurylether was heated and dissolved in ethanol, then water was added and dispersion was caused by a disperser. When adding a water-swelling viscous mineral, this was added to the mixture and dispersion further caused by a disperser. The oil component was added to this and dispersion was sufficiently caused by a disperser.

TABLE I-3

| | Sample No. | | | | |
|---|---|---|---|---|---|
| | 1 | 2 | 3 | 4 | 5 |
| Dimethyl polysiloxane | 81 *1 | 6 *3 | 20 *1 | 7 *3 | 77 *2 |
| Perfluoro polyether (FOMBLIN HC25) | — | 2 | — | — | — |
| Silica-alumina | 1 *4 | 1 *4 | 0.2 *4 | 12 *4 | 1 *4 |
| Water | 11 | 78.5 | 73.8 | 70 | 14 |
| Polyoxyethylene (15 mole) lauryl ether | 2 | 0.5 | 1 | 1 | 2 |
| Ethanol | 3 | 8 | 5 | 10 | 4 |
| Water-swelling clay mineral | 2 | 4 | — | 1 | 2 |
| Polyvinyl alcohol | | 1 | | | |
| Preservative | *6 | *6 | *6 | *6 | *6 |

*1: KF96A300
*2: KF96A100
*3: KF96A1000
*4: Silica (Aerosil R972)
*5: Alumina (Alumina AKS)
*6: Suitable quantity Next, the lipstick overcoats of Sample Nos. 1 to 5 were evaluated as to their lipstick mark prevention effect and sustainability of cosmetic effect plus ease of use by test methods similar to those explained above. The results of the evaluation are shown in Table I-4.

TABLE I-4

| | Sample No. | | | | |
|---|---|---|---|---|---|
| | 1 | 2 | 3 | 4 | 5 |
| Lipstick mark prevention effect | <1> | ○ | Δ | <2> | ○ |
| Sustainability of cosmetic effect | | ○ | Δ | | ○ |
| Ease of use | | ○ | Δ | | Δ |

<1> Emulsification impossible, overcoat could not be prepared.
<2> Aqueous phase becomes hard and homogeneous application not possible.

As clear from the results shown in Table I-3, Sample No. 3 exhibited a superior effect in each of the lipstick mark prevention effect, sustainability of the cosmetic effect, and ease of use even when using two types of dimethyl polysiloxane and perfluoro polyether.

Further, it was learned that the overcoats comprised of dimethyl polysiloxane and/or perfluoro polyether included in the range of the present invention (2 to 80 wt %) (result of evaluation of examples above) were superior to those outside the range (the above-mentioned Comparative Example I-3 and Sample No. 1).

Further, it was learned that an amount of silica powder and/or alumina powder as shown by the results of Sample Nos. 3 and 4 is somewhat effective, but that blending of 0.5 to 10% by weight is even more superior in effect.

Examples II-1 to II-6 and Comparative Examples II-1 to II-3, II-5, and II-6

The lipstick overcoats of the compositions shown in Table II-1 were prepared by the following method:

Example II-1 to Example II-6

Silica was moistened and made to disperse in ethanol. At that time, the amount of silica added was 1% for both of Example II-4 and Example II-5 (note that, as explained later, the remaining silica was made to disperse in the oil phase). Next, a water-swelling clay mineral was added and the mixture sufficiently stirred by a disperser to obtain a water phase.

The oil phase was prepared by adding polyether-modified silicone oil into dimethyl polysiloxane and then sufficiently stirring in a disperser. Note that in Example II-4 and Example II-5, the remaining silica was added and the mixture stirred. The stirring was continued by the disperser while adding the above water phase to cause full emulsification.

Comparative Example II-1 and II-2

Polyether-modified silicone oil was dispersed in an oil component. Water was gradually added to this, with stirring, to cause emulsification.

Comparative Example II-3

Silica and water-swelling clay minerals were moistened and made to disperse in ethanol, then water was added, further water-swelling clay minerals were added. The mixture was sufficiently stirred in a disperser.

Comparative Examples II-5 and II-6

The same procedures were followed as in Example II-1 to prepare lipstick overcoats.

TABLE II-1

| | Comparative Example | | | | | Example | | | | | |
|---|---|---|---|---|---|---|---|---|---|---|---|
| | II-1 | II-2 | II-3 | II-5 | II-6 | II-1 | II-2 | II-3 | II-4 | II-5 | II-6 |
| Dimethyl polysiloxane (KF96A-100) | 50 | — | — | 26 | 75 | 50 | —0 | 40 | 60 | 70 | 50 |
| Dimethyl polysiloxane (KF96A-1000) | — | 50 | — | — | — | — | 50 | — | — | — | — |
| Silica (Aerosil R972) | — | — | 1 | 0.7 | 2 | 2 | 2 | 2 | 1.5 | 3 | 0.6 |
| Water | 48 | 48 | 91 | 66.8 | 14.5 | 37 | 37 | 47 | 16.5 | 13.5 | 38.4 |
| Polyether-modified silicone oil | 2 | 2 | — | 1.5 | 1.5 | 2 | 2 | 2 | 2 | 1.5 | 2 |
| Ethanol | — | — | 5 | 3 | 5 | 5 | 5 | 5 | 5 | 5 | 5 |

TABLE II-1-continued

|  | Comparative Example | | | | | Example | | | | | |
| --- | --- | --- | --- | --- | --- | --- | --- | --- | --- | --- | --- |
|  | II-1 | II-2 | II-3 | II-5 | II-6 | II-1 | II-2 | II-3 | II-4 | II-5 | II-6 |
| Water-swelling clay mineral | — | — | 3 | 2 | 2 | 4 | 4 | 4 | 5 | 7 | 4 |
| Preservative | *1 | *1 | *1 | *1 | *1 | *1 | *1 | *1 | *1 | *1 | *1 |

*1: Suitable quantity

Comparative Example II-4

A lipstick overcoat was produced by the following formula and the following production method:

|  |  | (wt %) |
| --- | --- | --- |
| (1) | Perfluoro polyether (FOMBLIN HC-25) | 98.8 |
| (2) | Silica (Aerosil 300) | 1.0 |
| (3) | Red No. 202 | 0.1 |
| (4) | Flavor | 0.1 |

Method of Production

The components (2) to (4) were added to the component (1) and homogeneously mixed to produce a lipstick overcoat.

The lipstick mark prevention effect and sustainability of the cosmetic effect plus the ease of use of the lipstick overcoats of Examples II-1 to II-6 and Comparative Examples II-1 to II-6 were evaluated by the test methods mentioned above. The results of the evaluation are shown in Table II-2.

TABLE II-3

|  | Sample No. 1 | Sample No. 2 |
| --- | --- | --- |
| Dimethyl polysiloxane (KF96A-100) | 50 | 50 |
| Silica (Aerosil R972) | 0.4 | 11 |
| Water | 39.6 | 29.0 |
| Polyether-modified silicone oil | 2 | 2 |
| Ethanol | 6 | 6 |
| Water-swelling clay mineral | 2 | 2 |
| Preservative | Suitable quantity | Suitable quantity |

Sample Nos. 1 and 2 were evaluated in the same way as with the above Table II-2.

TABLE II-2

|  | Comparative Example | | | | | | Example | | | | | |
| --- | --- | --- | --- | --- | --- | --- | --- | --- | --- | --- | --- | --- |
|  | II-1 | II-2 | II-3 | II-4 | II-5 | II-6 | II-1 | II-2 | II-3 | II-4 | II-5 | II-6 |
| Lipstick mark prevention effect | x | x | ○ | ○ |  | Δ | ○ | ○ | ○ | ○ | ○ | Δ |
| Sustainability of cosmetic effect | x | x | Δ | ○ | <4> | x | ○ | ○ | ○ | ○ | ○ | Δ |
| Ease of use | ○ | Δ <1> | x <2> | x <3> |  | x <5> | ○ | Δ <1> | ○ | ○ | ○ | ○ |

<1> Somewhat heavy
<2> Low viscosity and repulsion from lipstick
<3> Separation and white specks appearing on lipstick
<4> w/o cannot be made and preparation impossible
<5> Low viscosity and dripping, so effect not good.

As clear from the results shown in Table II-2, the present embodiment is superior in each of the lipstick mark prevention effect, sustainability of the cosmetic effect, and ease of use.

Further, an investigation was made of the relation between the content of the dimethyl polysiloxane shown in the general formula (I) and various properties.

Compared with a content outside the scope of the present invention (Comparative Examples II-5 and II-6), it was learned that there is a remarkable effect in the range of the present invention (Examples).

Further, an investigation was made of the relationship between the content of the silica powder and/or alumina powder and the various properties using the Sample Nos. 1 and 2.

The results are shown in Table II-4.

TABLE II-4

|  | Sample No. 1 | Sample No. 2 |
| --- | --- | --- |
| Lipstick mark prevention effect | Δ | <1> |
| Sustainability of cosmetic effect | Δ |  |
| Ease of use | Δ |  |

<1> The viscosity of the aqueous phase became higher and emulsification became impossible. The overcoat therefore could not be prepared.

From the results of Table II-4, it is learned that an overcoat with a content of silica powder and/or alumina powder of less than 0.5% by weight is somewhat inferior in effect compared with one of 0.5% by weight to 10% by weight, but is improved in effect from Comparative Examples II-1 to II-6.

According to the present invention, as explained above, it is possible to provide a lipstick overcoat composition which can improve the sustainability of the cosmetic effect, suppresses lipstick marks, is superior in ease of use, and, further, is free from the problem of just perfluoropolyether coming out when squeezing the overcoat out of the tube and from the separation of the silica powder over time after application on the lipstick and the resultant appearance of white specks on the lipstick.

We claim:

1. An oil-in-water type emulsion lipstick overcoat composition comprising:

(i) 2 to 80% by weight of at least one compound selected from the group consisting of:

(a) dimethyl polysiloxanes having the formula (I):

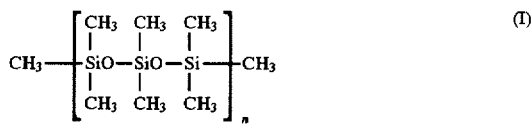

wherein n is 26–600 on average, and (b) perfluoro polyethers having the formula (II):

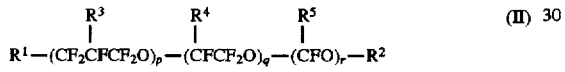

wherein, $R^1$, $R^2$, $R^3$, $R^4$, and $R^5$ are the same or different and represent a fluorine atom, a perfluoroalkyl group, or an oxyperfluoroalkyl group and p, q, and r are independently integers of 0 or more giving a molecular weight of 500 to 10,000, provided that p=q=r=0 never occurs, in an inner oil phase; and (ii) (a) water and (b) 0.5 to 10% by weight of at least one powder selected from the group consisting of silica powder and alumina powder in an outer water phase.

2. A water-in-oil type emulsion lipstick overcoat composition comprising:

(i) 40 to 70% by weight of dimethyl polysiloxane having the formula (I)

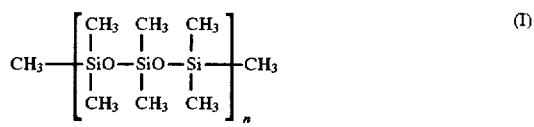

wherein n is 26–600 on average, in an outer oil phase; and (ii) (a) water and (b) 0.5 to 10% by weight of at least one powder selected from the group consisting of silica powder and alumina powder in an inner water phase.

* * * * *

UNITED STATES PATENT AND TRADEMARK OFFICE
CERTIFICATE OF CORRECTION

PATENT NO. : 5,750,094
DATED : May 12, 1998
INVENTOR(S) : Tomomasa, et al.

It is certified that error appears in the above-indentified patent and that said Letters Patent is hereby corrected as shown below:

ON THE TITLE PAGE:

Item [30] Foreign Application Priority Data:
Delete " May 24, 1994 " and substitute
-- May 25, 1994 --

Signed and Sealed this

Twenty-seventh Day of October, 1998

Attest:

BRUCE LEHMAN

*Attesting Officer*   *Commissioner of Patents and Trademarks*